(12) United States Patent
De et al.

(10) Patent No.: US 6,180,093 B1
(45) Date of Patent: Jan. 30, 2001

(54) METHOD AND COMPOSITION FOR REWETTING CONTACT LENSES AND RELIEVING EYE DRYNESS

(75) Inventors: Nimai C. De, deceased, late of Rochester; by Alice W. De, executrix, Buffalo; Yeshwant Sanzgiri; Irene Moran, both of Penfield, all of NY (US)

(73) Assignee: Bausch & Lomb Incorporated, Rochester, NY (US)

( * ) Notice: Under 35 U.S.C. 154(b), the term of this patent shall be extended for 0 days.

(21) Appl. No.: 08/915,708

(22) Filed: Aug. 21, 1997

Related U.S. Application Data

(60) Provisional application No. 60/031,480, filed on Sep. 20, 1996.

(51) Int. Cl.⁷ .................. A61K 31/74; A61K 31/155; A01N 37/52
(52) U.S. Cl. .................. 424/78.04; 514/635; 514/912; 514/915
(58) Field of Search .................. 424/78.04; 514/912, 514/915, 635

(56) References Cited

U.S. PATENT DOCUMENTS

| | | | |
|---|---|---|---|
| 3,428,576 | 2/1969 | Dickinson | 260/2 |
| 3,920,810 | 11/1975 | Rankin | 424/80 |
| 4,120,949 | 10/1978 | Bapatla | 424/80 |
| 4,323,467 | 4/1982 | Fu | 252/106 |
| 4,758,595 | 7/1988 | Ogunbiyi | 514/635 |
| 4,786,436 | 11/1988 | Ogunbiyi | 252/352 |
| 4,836,986 | * 6/1989 | Ogunbiyi et al. | 422/28 |
| 5,389,383 | * 2/1995 | Huth | 424/650 |
| 5,471,817 | * 12/1995 | Baker et al. | 53/429 |
| 5,591,426 | * 1/1997 | Dabrowski et al. | 424/78.04 |
| 5,741,817 | * 4/1998 | Chowhan et al. | 514/561 |
| 5,767,143 | * 6/1998 | Lehmussaari et al. | 514/397 |

FOREIGN PATENT DOCUMENTS

| | | | |
|---|---|---|---|
| 3007397A | 3/1981 | (DE) | G02C/13/00 |
| 83/01003 | 3/1983 | (WO) | A61K/31/74 |
| 94/06479 | 3/1994 | (WO) | A61L/2/18 |

OTHER PUBLICATIONS

Article entitled Poly (hexamethylenebiguanide hydrochloride), a novel cationic complexating agent for the assay of acidic polysaccharides by John F. Kennedy, S. Alan Barker and Ian J. Bradshaw.
Biochemical Society Transaction vol. 10 pp. 136–137 (1982).

* cited by examiner

Primary Examiner—Thurman K. Page
Assistant Examiner—T. Ware
(74) Attorney, Agent, or Firm—Robert B. Furr, Jr.

(57) ABSTRACT

The present invention is directed to a lubricant for contact lenses or dry eye or to provide relief from eye irritation. In particular, the composition contains a biguanide preservative in combination with polyvinylpyrollidone. An ophthalmic solution containing such a combination of components can be applied, in the form of droplets, to the eye or to contact lens in the eye. In one embodiment of the invention, the composition is used as a universal lubricant, meaning that the same solution can be used with or without contact lenses, depending on the needs of the user, whether in the context of a contact-lens care or general eye care.

1 Claim, No Drawings

METHOD AND COMPOSITION FOR REWETTING CONTACT LENSES AND RELIEVING EYE DRYNESS

This appln claims the benefit of U.S. Provisional No. 60/031,480 filed Sep. 20, 1996.

FIELD OF THE INVENTION

This invention relates to a composition and method for rewetting and lubricating contact lenses. In particular, the composition is an ophthalmic solution comprising the combination of a biguanide preservative and a polyvinylpyrrolidone demulcent. The composition is also useful for relieving eye dryness or irritation.

BACKGROUND OF THE INVENTION

Contact lenses in wide use today fall into two categories. First, there are the hard or rigid corneal type lenses that are formed from materials prepared by the polymerization of acrylic esters, such as polymethylmethacrylate (PMMA). Secondly, there are the gel, hydrogel or soft type of lenses made by polymerizing such monomers as 2-hydroxyethyl methacrylate (HEMA).

Solutions that wet the lenses before insertion in the eye are required for both the hard and soft types of contact lenses. After the contact lenses are inserted in the eye, ophthalmic solutions for rewetting, lubricating, and/or enhancing wearer comfort are sometimes applied to the eye by means of an eye dropper.

Wetting or rewetting solutions usually contain a wetting agent in combination with a germicide or preservative, a viscosity builder, and salts that adjust the tonicity of the solutions to make them compatible with the osmolality of tear fluids. Such a wetting solution, for example, is disclosed in U.S. Pat. No. 4,323,467.

The hard acrylic type of contact lenses are highly durable and, since they do not absorb appreciable amounts of water, the selection of a suitable disinfecting agent or other chemical agent for lens care is relatively non-critical. Unlike hard lenses, however, the soft type of contact lenses have a significant tendency to bind and concentrate the antimicrobial agents found in lens-care solutions. This tendency can be exacerbated by the inherent binding action of any protein deposits on the lenses. Soft lenses are more susceptible to protein deposits and, hence, more susceptible to the binding of various antimicrobial agents.

Thus, in spite of low toxicity levels, not all disinfectants are compatible for use with all types of contact lenses. Many disinfecting and preservative solutions for hard lenses contain benzalkonium chloride. Although it is an effective antibacterial agent, it is incompatible and should not be used with soft contact lenses, because it is taken up by the lens. Severe toxicity may occur due to sustained release of benzalkonium chloride from the lens. Thimerosal, or sodium ethylmercurithiosalicylate, was introduced as an alternative to benzalkonium chloride, but is also incompatible with soft lenses.

Antibacterial agents must be selected that do not build up on lens surfaces and do not become concentrated to potentially harmful levels, such that corneal inflammation or other eye irritation results. Previous efforts to alleviate the problem of binding and concentrating of disinfectants and preservatives onto contact lens surfaces and to reduce the potential for eye tissue irritation have not been totally satisfactory.

Sorbic acid is less irritating than mercurials and has experienced some popularity as a preservative. However, it reportedly may increase age-associated yellowing of some lenses, particularly those containing methacrylic acid or the like.

Various biguanides have been found to exhibit good compatibility with soft contact lenses and have been used as a germicide in some contact-lens solutions. U.S. Pat. No. 4,758,595 discloses the use of biguanides in a multi-purpose contact-lens cleaning solution that does not include any polymeric demulcents. U.S. Pat. No. 4,786,436 discloses a wetting solution which discloses the use of a biguanide or water soluble salt thereof, in combination with collagen and other demulcents such as hydroxylethyl cellulose, methyl cellulose, carboxymethyl cellulose, hydroxypropyl methyl cellulose, hydroxylpropylcellulose and the like. However, whether due to instability or incompatibility of the biguanide in general eye care formulations, or for some other problem or deficiency, biguanides have not been commercially used in eye-drop solutions. Some past studies have suggested that the biguanides known as PAPB or PHMB (polyhexamethylene biguanide or its salt) exhibited poor stability or loss of preservative efficacy in small volume containers. Originally, it was thought that this problem may have been due to an undesirable interaction of the biguanide with the plasticizer present in the LDPE (low density polyethylene) material used to make squeeze bottles that typically hold eye-drop solutions.

It is also known that biguanides may undesirably react with certain polymers in solution. For example, Kennedy, J. F. et al., "The Assay of Acidic Polysaccharides in Solution with Poly(Hexamethylenebiguanidinium choloride)," *Carbohydrate Research*, 156 (1986) at 79–85 discloses that the biguanide known as PHMB complexes with and even precipitates carboxylated and sulphated polysaccharides.

A variety of polymers are known as demulcents in the field of ophthalmic products, including carboxymethyl cellulose sodium, hydroxyethyl cellulose and other cellulose derivatives, dextran, gelatin, and polyols such as glycerin, polyethylene glycol, polysorbate, propylene glycol, polyvinyl alcohol, and povidone. U.S. Pat. No. 4,120,949 discloses the use of polyvinylpryrrolidone, or povidone, as a demulcent. Rankin, in U.S. Pat. No. 3,920, 810, discloses the use of polyvinylpyrrolidone (PVP) as a demulcent and lubricant in solutions used to treat dry eye. PVP is known to act as a demulcent lubricant by means of a combination of adhesive and lubricating properties that aid in the spreading of its viscous solution. PVP, however, is also known to be incompatible with a wide variety of inorganic salts and other chemicals. See, for example, Wade, A. et al, ed., *Handbook of Pharmaceutical Excipients*, 2d Ed. (American Pharmaceutical Association, Washington 1994) at p. 396. The efficacy of some preservatives, e.g. thimerosal, may be adversely affected by the formation of complexes with PVP.

It would be desirable to provide an eye-drop solution for wetting and lubricating lenses that is formulated using a biguanide preservative, without any loss of efficacy, thereby allowing the replacement of sorbic acid or benzalkonium chloride with a biguanide which is inherently less irritating to the eye. Furthermore, it would be desirable to provide an eye-drop solution that can be safely and efficaciously used for both lubricating contact-lens in the eye and, irrespective of whether contact lenses are being worn, for treating dry eye or for soothing eye irritation.

SUMMARY OF THE INVENTION

The present invention is directed to a lubricant for contact lenses or dry eye comprising an aqueous solution containing a biguanide preservative in combination with polyvinylpyrrolidone. An ophthalmic solution containing such a combination of components can be applied in the form of droplets, optionally while a contact lens is in the eye. The invention may comprises a system useful as an artificial tear or for rewetting or lubricating contact lenses while in the eye, said system comprising a an eye-drop dispenser and a plastic container holding between about 1 and about 30 mL of an ophthalmic solution that comprises:

(a) an effective germicidal amount of a biguanide;

(b) polyvinylpyrrolidone which is present in an amount of 0.01 to 10.0% by weight;

(c) at least one tonicity agent which is present in an amount of 0.01 to 10.0% by weight;

(d) a sequestering agent which is present in an amount of 0.01 to 10.0% by weight;

(e) an effective amount of a buffering agent; and (f) water.

The invention is also directed to a method of using the foregoing composition. The objects, features, and advantages of the various embodiments of the present invention will become more readily apparent from the following detailed description.

DETAILED DESCRIPTION OF THE INVENTION

The present invention is directed to an ophthalmic solution useful for rewetting or lubricating lenses. It can also be used as a universal lubricant, meaning that the same formulation or bottled solution can be used equally well for treating dry eye, eye irritation, or the like, whether or not the user is wearing contact lenses.

While the present invention can be used in connection with a variety of soft lenses, it is especially useful with respect to hydrophilic lenses made from polymers having repeats units derived from hydroxyethyl methacrylate monomers, and especially lenses made from polymers having additional repeat units derived from methacrylic acid. Group III and Group IV lenses (FDA categories) often contain methacrylic acid monomers. Group IV is distinguished from Groups I to III by having (with respect to Group I and III) higher water content and (with respect to Group I and II) being more ionic. Typically, Group IV lenses have a water content greater than 50% by weight. High water content is associated with materials having high oxygen permeability, resulting in the increasing popularity of Group IV lenses, especially disposable and frequent-replacement lenses. Such materials include, but are not limited to, bufilcon A, etafilcon A, methafilcon A, ocufilcon C, perfilcon A, phemfilcon A, and vifilcon A. Materials containing methacrylic acid monomers include methafilcon B, ocufilcon D, methafilcon A, and etafilcon A (USAN and the USAP Dictionary of Drug Names). Lenses made from the foregoing materials are commercially available from a variety of sources. Such lenses include daily-wear lenses, extended-wear lenses, planned-replacement lenses, and disposable lenses.

The ophthalmic solution of the invention, whether for use as an artificial tear or as lubricant for contact lens, or both, requires the combination of polyvinylpyrrolidone and a biguanide. The PVP provides tear film stability and wetting of the corneal surfaces and also allows the use of the biguanide in effective preservative concentrations in the solution.

The polyvinylpyrrolidone (PVP) used in the compositions of the invention is a linear homopolymer or essentially a linear homopolymer comprising at least 90% repeat units derived from 1-vinyl-2-pyrrolidone monomers, the polymer more preferably comprising at least about 95% or essentially all of such repeat units, the remainder selected from polymerization-compatible monomers, preferably neutral monomers, such as alkenes or acrylates. Other synonyms for PVP include povidone, polyvidone, 1-vinyl-2-pyrolidinone, and 1-ethenyl-2-pyrolionone (CAS registry number 9003-39-8). The PVP used in the present invention suitably has a weight average molecular weight of about 10,000 to 250,000, preferably 30,000 to 100,000. Such materials are sold by various companies, including ISP Technologies, Inc. under the trademark PLASDONE™ K-29/32, BASF under the trademark KOLLIDON™ for USP grade PVP, for example KOLLIDON™ K-30 or K-90. It is to be understood, however, that the invention is not limited to any specific PVP and that any equivalent PVP of acceptable purity for ophthalmic use, preferably pharmaceutical grade, may be used.

In the present compositions, polyvinylpyrrolidone is suitably present in an amount 0.01 to 10.0% by weight, preferably of between 0.05 to 5.0 percent by weight.

The present composition will contain a disinfecting amount of a biguanide as an antimicrobial agent. As used herein, antimicrobial agents are defined as organic chemicals which derive their antimicrobial activity through a chemical or physiochemical interaction with the microbial organisms. Biguanides include the free bases or salts of alexidine, chlorhexidine, hexamethylene biguanides and their polymers, and combinations of the foregoing.

The salts of alexidine and chlorhexidine can be either organic or inorganic and are typically gluconates, nitrates, acetates, phosphates, sulphates, halides and the like. Preferred antimicrobial agents are the polymeric quaternary ammonium salts used in ophthalmic applications and the biguanides. More preferred are the biguanides and hexamethylene biguanides (commercially available from Zeneca, Wilmington, Del. under the trademark Cosmocil™ CQ), their polymers and water-soluble salts being most preferred. Generally, the hexamethylene biguanide polymers, also referred to as polyaminopropyl biguanide (PAPB), have molecular weights of up to about 100,000. The term polyhexamtheylene biguanide, as used herein, is meant to encompass one or more biguanides have the following formula:

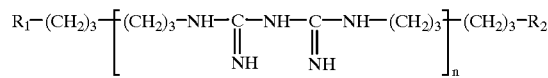

wherein n is from 1 to 500 and the end groups $R_1$ and $R_2$ are independently —$NH_2$ or

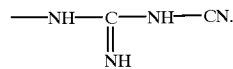

Depending on the manner in which the biguanides are prepared, the predominant compound falling within the above formula may have different $R_1$ and $R_2$ groups or the same groups, with lesser amounts of other compounds within the formula. Such compounds are known and are disclosed in U.S. Pat. No. 4,758,595 and British Patent 1,432,345, which patents are hereby incorporated herein by reference. The antimicrobial agents used herein are preferably employed in the absence of mercury-containing compounds such as thimerosal, although the solutions may also include other conventional germicidal agents that are not incompatible with the biguanides.

The biguanides are much more effective against the various organisms than other disinfectants such as sorbic acid, particularly when used at low concentrations. The biguanides can be low molecular weight oligomers where n in the above formula averages from 4 to 10, high molecular weight long chain polymers up to 100,000 weight average molecular weight, as well as individual monomers of such polymers where n is 1. The biguanides also include the water-soluble salts of the free bases, such as hydrochloride and borate salts, acetate, gluconate, sulfonate, tartrate and citrate salts. Preferably, the water-soluble salts are compounds where n has a value of 2 to 12, most preferably 3 to 8. One preferred group of water-soluble biguanides have an average molecular weight of at least 1,000 and more particularly from 1,000 to 50,000.

The biguanides demonstrate less binding and lower toxicity levels than other disinfectants. Also, monomers, such as hexamethylene biguanide hydrochloride, provide good bactericidal activity at low concentrations with little binding effect, as does polyhexamethylene biguanide hydrochloride wherein n is 4 to 10.

U.S. Pat. No. 3,428,576 describes the preparation of biguanides from a diamine and salts thereof and a diamine salt of dicyanimide. This patent teaches methods for making the hydrochloride salt of polyhexamethylene biguanide which, however, as mentioned above, is commercially available from Zeneca, Inc. under the trademark Cosmocil® CQ. This biguanide is often referred to as either "PHMB" or "PAPB," as herein, usually by the latter acronym corresponding to polyaminopropyl biguanide.

One or more biguanides may be used with other known preservatives, in various combinations. For example, the combination of PAPB and chlorhexidine is known for use in lens-care solutions for rigid gas permeable lenses.

The solutions of this invention can be prepared by a variety of techniques. One method includes the preparation of a PVP-containing solution by initially heating about 80 percent of the distilled water to be used, to 80° C. With agitation, the alkali metal chlorides, sequestering agents, buffering agents, and surfactants are added. After the solution is cooled to room temperature, the PAPB is added, followed by the balance of distilled water. The solution can then be sterilized by forcing it through an 0.22 micron cellulose acetate filter by means of a peristaltic pump, followed by packaging in sterilized plastic containers.

The preservative efficacy of the solutions can be tested by exposing S. aureus ($1 \times 10^6$ microorganisms/ml), P. aeruginosa ($1 \times 10^6$ microorganisms/ml), E. coli ($1 \times 10^6$ microorganisms/ml) C. albicans ($1 \times 10^6$ microorganisms/ml) and A. nigeri ($1 \times 10^6$ microorganisms/ml) each to 20 ml of the solution at room temperature for 14 days. Subsequently, an aliquot sample of each is placed on an agar plate and incubated for 48 hours at elevated temperatures. At the conclusion of the incubation period, the plates are examined for the development of colonies.

A disinfecting amount of the biguanide antimicrobial agent is an amount which will at least partially reduce the microorganism population in the formulations employed. Preferably, a disinfecting amount is that which will reduce the microbial burden by a certain number of log orders within a certain period of time, depending on the particular microorganism involved. Typically, such agents are present in concentrations ranging from about 0.00001 to about 0.10% by weight, and more preferably, from about 0.0001 to about 0.001% by weight.

The solutions of this invention will also contain water and one or more other components which are commonly present in contact lens care solutions. In addition to the active ingredients described above, solutions according to the present invention may contain buffers, various cleaners, stabilizers, isotonic agents and the like which aid in making ophthalmic compositions more comfortable to the user. The aqueous solutions of the present invention are typically adjusted with tonicity agents to approximate the osmotic pressure of normal lacrimal fluids which is equivalent to a 0.9% solution of sodium chloride or 2.5% of glycerol solution. The solutions are made substantially isotonic with physiological saline used alone or in combination, otherwise if simply blended with sterile water and made hypotonic or made hypertonic the lenses will lose their desirable optical parameters. Correspondingly, excess salt or other tonicity agent may result in the formation of a hypertonic solution which will cause stinging and eye irritation. An osmolality of about 225 to 400 mOsm/kg is preferred, more preferably 280 to 320 mOsm/kg.

Solutions used for rewetting lubricating contact lens while the lens is in the eye sometimes include a surfactant to loosen deposits on the lens; wherein removal is assisted by the natural cleaning action of blinking. Any surfactant that is known to be useful in contact wetting solutions can be used in the solutions of this invention. The surfactant should be soluble in the lens care solution, non-irritating to eye tissues and usually have a hydrophilic-lipophile balance (HLB) of 12.4 to 18.8. Satisfactory non-ionic surfactants include polyethylene glycol esters of fatty acids, e.g. coconut, polysorbate, polyoxyethylene or polyoxypropylene ethers of higher alkanes ($C_{12}$–$C_{18}$). Examples of the preferred class include polysorbate 20 (available from ICI Americas Inc., Wilmington, Del. 19897 under the trademark Tween® 20), polyoxyethylene (23) lauryl ether (Brij® 35), polyoxyethylene (40) stearate (Myrj® 52), polyoxyethylene (25) propylene glycol stearate (Atlas® G2612). Brij® 35, Myrj® 52 and Atlas® G 2612 are trademarks of, and are commercially available from, ICI Americas Inc., Wilmington, Del. 19897.

One non-ionic surfactant in particular, consisting of a poly(oxypropylene)-poly(oxyethylene) adduct of ethylene diamine having a molecular weight from about 7,500 to about 27,000 wherein at least 40 weight percent of said adduct is poly(oxyethylene), has been found to be particularly advantageous for use in conditioning contact lenses when used in amounts from about 0.01 to about 15 weight percent. The CTFA Cosmetic Ingredient Dictionary's adopted name for this group of surfactants is poloxamine. Such surfactants are available from BASF Wyandotte Corp., Wyandotte, Mich., under the registered trademark "Tetronic". An analogous series of surfactants is the poloxamer series which is a polyoxyethylene, polyoxypropylene block polymer available from BASF Wyandotte Corp., Parsippany, N.J. 07054 under the trademark "Pluronic".

Amphoteric, polyquaternium and nonionic surfactants suitable for use in the invention can be readily ascertained, in view of the foregoing description, from McCutcheon's Detergents and Emulsifiers, North American Edition, McCutcheon Division, MC Publishing Co., Glen Rock, N.J. 07452.

As indicated above, PVP is used in the present invention as a demulcent that can be advantageously combined with a biguanide. The PVP provides wetting, moisturizing, and/or lubricating of contact lens in the eyes of wearers, resulting in their increased comfort. The PVP also serves to provide for the soothing or relief of dry eye or eye irritation. PVP also acts as a water-soluble viscosity builder. Additional viscosity builders or demulcents may optionally be included in the present composition, in combination with PVP, for example, polyvinyl alcohol, cellulose derivatives, glycerin, and the like. Such viscosity builders or demulcents may be employed in a total amount ranging from about 0.01 to about 5.0 weight percent or less. Suitably, the viscosity of the final formulation is 10 cps to 50 cps.

The pH of the present solutions should be maintained within the range of 5.0 to 8.0, more preferably about 6.0 to 8.0, most preferably about 6.5 to 7.8, suitable buffers may be added, such as boric acid, sodium borate, potassium citrate, citric acid, sodium bicarbonate, TRIS, and various mixed phosphate buffers (including combinations of $Na_2HPO_4$, $NaH_2PO_4$ and $KH_2PO_4$) and mixtures thereof Borate buffers are preferred, particularly for enhancing the efficacy of PAPB. Generally, buffers will be used in amounts ranging from about 0.05 to 2.5 percent by weight, and preferably, from 0.1 to 1.5 percent.

In addition to buffering agents, in some instances it may be desirable to include sequestering agents in the present solutions in order to bind metal ions which might otherwise react with the lens and/or protein deposits and collect on the lens. Ethylene-diaminetetraacetic acid (EDTA) and its salts (disodium) are preferred examples. They are usually added in amounts ranging from about 0.01 to about 0.2 weight percent.

As indicated above, the present invention is also useful for relieving eye irritation or dryness and providing lubrication for the eyes, irrespective of whether contact lenses are present in the eyes of the user. Thus, as mentioned above, compositions of the present invention can function as artificial tears and can be used, as needed, for the temporary relief of eye irritation of discomfort. For example, many people suffer from temporary or chronic eye conditions in which the eye's tear system fails to provide adequate tear volume or tear film stability necessary to remove irritating environmental contaminants such as dust, pollen, or the like. In persons suffering from chronic "dry eye," the film on the eye tends to becomes discontinuous. Because of their emollient and lubricating effect, artificial tears can be used to soothe the eye.

Some artificial tears that have been on the market are not recommended for use with lenses in place. An advantage of one embodiment of the present invention is that the compositions can be used with or without the lenses in place, so that a single product may take the place of two separate products. Such a product is referred to as a universal lubricant.

Finally, a composition according to the present invention can also be used as a carrier for ophthalmic solutions that include pharmaceutical compounds. For example, the composition can be used to make allergy drops with the addition of an effective amount of naphazoline hydrochloride.

The compositions of the present invention are typically sold in a wide range of small volume containers from 1 to 30 mL in size, preferably 1 mL to 20 mL in size. Such containers can be made from HDPE (high density polyethylene), LDPE (low density polyethylene), polypropylene, poly(ethylene terephthalate) and the like. Flexible bottles having conventional eye-drop dispensing tops are especially suitable for use with the present invention.

Compositions according to the present invention can be applied as follows. During wear, about two or three drops are placed directly onto each lens whenever needed. Thereafter, the wearer should blink several times. After waiting a few moments, if the lens still does not feel comfortable, another drop can be added. In the case where the user is not wearing any contact lens, a solution according to the present invention may be similarly used by instilling about 1 or 2 drops in the affected eye(s) as needed, for the temporary relief of burning and irritation due to dryness in the eye and for use as a protectant against further irritation, or to relieve dryness to the eye.

The following specific experiments and examples demonstrate the compositions and methods of the present invention. However, it is to be understood that these examples are for illustrative purposes only and do not purport to be wholly definitive as to conditions and scope. All percentages are by weight of the solution, unless indicated otherwise.

EXAMPLE 1

An aqueous solution of the invention, useful as a universal lubricant, is prepared with the following ingredients:

TABLE 1

| Ingredient | mg/gm | % w/w |
|---|---|---|
| Polyhexamethylene Biguanide HCl (20% w/w solution) | 0.0047 | 0.00047 |
| Boric Acid | 64 | 0.64000 |
| Sodium Borate | 0.94 | 0.09400 |
| Sodium Cloride | 5.4 | 0.54000 |
| PVP-K90 (BASF) polyvinylpyrrolidone | 15.0 | 1.50000 |
| Edetate Disodium | 1.0 | 0.10000 |
| Sodium Hydroxide, 1N | qs to adjust | pH 7.0–7.2 |
| Hydrochloric Acid, 1N | qs to adjust | pH 7.0–7.2 |
| Purified Water qs. to | 1.0 gm | 100% |

The formulation is prepared in bulk as follows. In a 316-grade stainless steel jacketed pressure kettle equipped with agitation, purified water is added equivalent to 80% of the batch weight. The contents are heated to achieve and maintain a water temperature of 80±5° C. Agitation is initiated and maintained throughout the entire processing of the batch. The batch quantities of boric acid, sodium borate, EDTA (Na$_2$), sodium chloride and PVP-K90 are added and dissolved. Upon dissolution of these components, the batch is charged with purified water to 98% of the final weight. The solution is mixed for a minimum of 10 minutes to ensure complete dissolution. If necessary, the pH is adjusted to 7.0–7.20 at 25° C. with 1N NaOH or 1N HCl. The solution is sterilized by autoclave at 121–124° C. for 30–45 minutes and then immediately cooled to 40° C. A stock solution of 1000 ppm of PAPB is prepared in water and filtered through a 0.22 micrometer cellulose acetate filter. Under sterile conditions, the calculated amount of stock solution of the PAPB is added to the previously prepared bulk solution containing PVP-K90. A sufficient quantity of cool purified water is added to obtain the final weight, and the entire solution is mixed for at least 15 minutes. For best product clarity, the finished solution should be ascepticially passed through a sterile 40–50 micrometer polishing filter. For use in the above process, suitable polishing filters include Pall Rigimesh™ RR40 micrometer and Filterite Dynalloy™ 30 micrometer PSP 12-10SL-M7. Suitable sterilizing filters include Millipore Millidisk™ MCGL 40S, 30S, 20S, and 10S.

EXAMPLE 2

An aqueous solution of the invention, useful for moisture drops, is prepared with the following ingredients:

TABLE 2

| Ingredient | mg/gm | % w/w |
|---|---|---|
| Polyhexamethylene Biguanide HCl (20% w/w solution) | 0.0047 | 0.00047 |
| Boric Acid | 3.0 | 0.30000 |
| Sodium Borate | 0.35 | 0.03500 |
| Sodium Chloride | 4.0 | 0.40000 |
| Potassium Chloride | 3.5 | 0.35000 |
| Edetate Disodium | 0.3 | 0.03000 |
| HPMC E15-LV hydroxypropylmethylcellulose | 5.0 | 0.50000 |
| PVP-K30 (BASF) polyvinylpyrolidone | 1.0 | 0.10000 |
| Glycerin | 2.0 | 0.20000 |
| Sodium Hydroxide, 1N | qs. to adjust | pH 7.1–7.5 |
| Hydrochloric Acid, 1N | qs. to adjust | pH 7.1–7.5 |
| Purified Water qs. q.s. to | 1.0 gm | 100% |

The formulation is prepared in bulk as follows. In a 316 stainless steel jacketed mixing vessel, water is added equivalent to 80% of the batch weight. The water is maintained at 80°±5° C. and with agitation are added sodium chloride, potassium chloride, sodium borate, boric acid, edetate disodium and HPMC E15-LV (hydroxypropylmethyl cellulose). After complete dissolution the batch is cooled to 50°±5° C. and PVP K30 and glycerin are added and dissolved. The batch is charged with purified water to bring it to 98% of final weight, cooled to 25° C. and mixed for at least 20 minutes. The pH is adjusted if needed to 7.1–7.5 using 1N NaOH or 1N HCl. The batch is transferred to sterile storage tank through a 0.22 micron sterilizing filter. A stock solution of 1000 PAPB in water is prepared and added to the batch in a calculated amount through 0.22 micron sterilizing filter. A sufficient amount of cool purified water is added to obtain final batch weight and the entire batch mixed for at least 15 minutes.

COMPARATIVE EXAMPLE

To examine the preservative efficacy of various biguanide-preserved lubricant formulations, the six lubricant formulations with key ingredients indicated in the Table below were prepared.

In the above Table, PVA and PVP K-90 are respectively conventional polyvinylalcohol polyvinylpyrolidone demulcents. A USP preservative efficacy test one each composition was performed as modified by FDA Draft Guidelines to include a microbial rechallenge. In brief, 20 mL of solution was challenged at ~1×10$^6$ cfu/mL with *Staphylococcus aureus* ATCC #6538. *Pseudomonas aeruginosa* ATCC #9027, *Escherichia coli* ATCC #8739, *Candida albicans* ATCC #10231 or *Aspergillus niger* ATCC #16404. Sampling of all solutions occurred at 7 days, 14 days, 21 days and 28 days following inoculation. The samples were rechallenged at ~1×10$^5$ cfu/mL with the challenge organism at day 14 after the sample was removed to determine surviving colony forming units. No neutralizer efficacy/toxicity testing was performed as PHMB levels are levels for which Dey-Engley Broth has been shown to be efficacious.

TABLE 3

| Ingredient | Example 16 mg/g | Example 17 mg/g | Comparative Example 18 mg/g | Example 19 mg/g | Comparative Example 20 mg/g | Comparative Example 21 mg/g |
|---|---|---|---|---|---|---|
| Borate buffer | + | + | — | — | — | — |
| Phosphate buffer | — | — | + | + | + | + |
| PVP K-90 | 15 | 15 | 5 | 5 | — | — |
| PVA | — | — | 10 | 10 | 15 | 15 |
| PHMB | 0.0018 | 0.0047 | 0.0018 | 0.0047 | 0.0018 | 0.0047 |

TABLE 4

| | | Log Reductions | | | | | |
|---|---|---|---|---|---|---|---|
| Organisms | Time point | Example 16 | Example 17 | Comparative Example 18 | Example 19 | Comparative Example 20 | Comparative Example 21 |
| *E. coli* | 7 days | 5.2 | >4.8 | 4.2 | >4.8 | 4.2 | >4.8 |
| | 14 days | >4.8 | >4.8 | >4.8 | >4.8 | >4.8 | >4.8 |
| | 21 days | >4.1 | >4.1 | >4.1 | >4.1 | >4.1 | >4.1 |
| | 28 days | >4.1 | >4.1 | >4.1 | >4.1 | >4.1 | >4.1 |
| *P. aeruginosa* | 7 days | >5.1 | >5.1 | 2.3 | 3.0 | 2.7 | 2.4 |
| | 14 days | >5.1 | >5.1 | 1.9 | 3.2 | 2.4 | 3.1 |
| | 21 days | >4.1 | >4.1 | 3.9 | 2.6 | 2.7 | >4.1 |
| | 28 days | >4.1 | >4.1 | 1.7 | 3.0 | 2.8 | 2.1 |
| *S. aureus* | 7 days | 3.4 | >4.8 | 4.3 | >4.8 | 4.2 | 5.1 |
| | 14 days | >4.8 | >4.8 | >4.8 | >4.8 | >4.8 | >4.8 |
| | 21 days | 2.6 | >4.1 | >4.1 | >4.1 | >4.1 | >4.1 |
| | 28 days | >4.1 | >4.1 | >4.1 | >4.1 | >4.1 | >4.1 |
| *C. albicans* | 7 days | 0.6 | 2.0 | 1.0 | 2.1 | 0.8 | 2.8 |
| | 14 days | 1.5 | 3.4 | 2.9 | 3.7 | 2.7 | 4.3 |
| | 21 days | 0.1 | 0.5 | 2.3 | 2.2 | 2.1 | 2.2 |
| | 28 days | 0.8 | 2.2 | 3.7 | 3.7 | 3.3 | 3.6 |
| *A. niger* | 7 days | 1.2 | 1.3 | −0.1 | −0.2 | 0.0 | 0.0 |
| | 14 days | 1.0 | 0.9 | 0.0 | −0.2 | 0.0 | −0.2 |
| | 21 days | 0.1 | 0.2 | −0.2 | −0.1 | −0.2 | −0.1 |
| | 28 days | 0.5 | 0.6 | −0.1 | 0.1 | 0.0 | 0.0 |

The results of the preservative efficacy studies are presented in Table 4. The negative controls (inoculated peptone samples) showed growth over the duration of the test and established the integrity of the organism preparations. By the criteria of the test: a) the concentrations of the bacteria (*S. aureus, P. aeruginosa* and *E. coli*) are reduced at least 3 logs from the original concentration, by day 14, b) the concentrations of the fungi (*C. albicans* and *A. niger*) remained at or below the original concentration during the first 14 days and c) the concentration of each test organism meets the same criteria by day 28, 14 days after rechallenge.

Three of the experimental formulations, Examples 16, 17 and 19 met the criteria to pass the test, whereas Examples 18, 20 and 21 failed the test. The formulations in Table 3 that passed had either a combination of a higher level of PAPB (0.0047 mg/g) with a lower level of PVP (5 mg/g) or a lower level of PAPB (0.0018 mg/g) with a higher level of PVP (15 mg/g). The formulations that failed the test had a combination of a lower level of PAPB with either a lower level or absence of PVP or a higher level of PAPB with an absence of PVP. This indicates that the combination of PVP and the PAPB is both efficacious and advantageous. Although the comparison between Examples 16 and Comparative 18 may be affected by the presence of a borate buffer, which is known to enhance the antimicrobial efficacy of PAPB, the advantage of the present composition is plainly indicated by a comparison between two compositions neither of which contained borate buffer, namely Example 19 and Comparative Example 21. The results help establish the advantageous relationship of PAPB and PVP, enhanced by borate, when used in adequate concentrations as outlined by this document.

What is claimed is:

1. An aqueous solution for treating dry eye, consisting of:
   (a) at least one antimicrobial agent, wherein the antimicrobial agent includes a biguanide antimicrobial agent;
   (b) at least one polyvinylpyrrolidone polymer;
   (c) at least one buffering agent;
   (d) at least one sequestering agent;
   (e) at least one tonicity agent and/or pH adjusting agent;
   (f) water; and
   (g) optionally, at least one surfactant.

* * * * *